United States Patent

Wu

(10) Patent No.: US 11,045,356 B2
(45) Date of Patent: Jun. 29, 2021

(54) WELDING HELMET HAVING A ZIPPER ARRANGEMENT AND WELDING HELMET ASSEMBLY

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 311 days.

(21) Appl. No.: 15/505,055

(22) PCT Filed: Sep. 1, 2015

(86) PCT No.: PCT/CN2015/088738
§ 371 (c)(1),
(2) Date: Feb. 17, 2017

(87) PCT Pub. No.: WO2017/000380
PCT Pub. Date: Jan. 5, 2017

(65) Prior Publication Data
US 2017/0281415 A1  Oct. 5, 2017

(30) Foreign Application Priority Data
Jul. 2, 2015 (CN) .......................... 201510383611.3

(51) Int. Cl.
*A61F 9/06* (2006.01)
*A41D 31/08* (2019.01)
(Continued)

(52) U.S. Cl.
CPC .......... *A61F 9/065* (2013.01); *A41D 13/0512* (2013.01); *A41D 31/08* (2019.02);
(Continued)

(58) Field of Classification Search
CPC .. A61F 9/065; A61F 9/06; A61F 9/062; A61F 9/064; A61F 9/067; A61F 9/068;
(Continued)

(56) References Cited

U.S. PATENT DOCUMENTS 3,825,952 A * 7/1974 Pershing ................ A42B 3/105
2/422
4,172,294 A * 10/1979 Harris .................... A62B 18/04
2/171.3

(Continued)

FOREIGN PATENT DOCUMENTS

CN  101081328 A   12/2007
CN  103623516 A   3/2014
(Continued)

OTHER PUBLICATIONS

State Intellectual Proper Office of the P.R. China, International Search Report of International Application No. PCT/CN2015/088738 (dated Apr. 1, 2016).

(Continued)

*Primary Examiner* — Jameson D Collier
*Assistant Examiner* — F Griffin Hall

(57) ABSTRACT

The present application relates to a welding helmet comprising a helmet housing and a head cover adapted to be worn on a wearer's head and made of an air-impermeable and flexible material, wherein a zipper arrangement is provided between the helmet housing and the head cover to detachably connect the head cover to the helmet housing around the whole perimeter of an opening of the helmet housing, and wherein after the head cover is connected to the helmet housing, the zipper arrangement is located within the housing of the welding helmet. The present application also relates to an assembly having the welding helmet.

15 Claims, 5 Drawing Sheets

(51) Int. Cl.
*A41D 13/05* (2006.01)
*A41H 37/00* (2006.01)
*A42B 3/10* (2006.01)

(52) U.S. Cl.
CPC ............ *A41H 37/003* (2013.01); *A42B 3/105* (2013.01); *A61F 9/06* (2013.01); *A61F 9/068* (2013.01); *A61F 9/067* (2013.01)

(58) Field of Classification Search
CPC ............ A41D 13/0512; A41D 31/0022; A41D 31/08; A41D 13/1153; A42B 3/105; A42B 3/10; A42B 3/04; A42B 3/00; A42B 3/225; A42B 3/228; A42B 3/24; A42B 3/28; A42B 3/288; A42B 3/281; A41H 37/003; A62B 17/04; A62B 18/02; A62B 18/025; A62B 18/04; A62B 18/045; A62B 18/08; A62B 18/084
USPC ..... 2/8.7, 8.2, 8.4, 8.5, 8.6, 8.8, 8.1, 7, 410, 2/5, 6.1, 6.2, 4, 455, 457, 421, 2.11
See application file for complete search history.

(56) References Cited

U.S. PATENT DOCUMENTS

| | | | | |
|---|---|---|---|---|
| 5,421,326 A * | 6/1995 | Rankin | ............ | A41D 13/0053 128/201.11 |
| 6,016,805 A * | 1/2000 | Burns | ............ | A42B 3/288 128/206.24 |
| 7,197,774 B2 * | 4/2007 | Curran | ............ | A62B 18/04 2/441 |
| 7,534,005 B1 * | 5/2009 | Buckman | ............ | A61F 9/068 2/8.2 |
| 7,631,364 B2 * | 12/2009 | Culler | ............ | A62B 17/006 2/2.17 |
| 8,104,094 B2 * | 1/2012 | Uttrachi | ............ | F16P 1/06 2/7 |
| 8,201,273 B2 * | 6/2012 | Duncan | ............ | A42B 1/008 2/202 |
| 8,336,113 B2 | 12/2012 | Uttrachi | | |
| 2005/0060788 A1 * | 3/2005 | Green | ............ | A41D 13/1153 2/171.3 |
| 2007/0277294 A1 | 12/2007 | Green | | |
| 2008/0040837 A1 | 2/2008 | King et al. | | |
| 2010/0154179 A1 * | 6/2010 | Blackford | ............ | A44B 19/32 24/399 |
| 2010/0287688 A1 * | 11/2010 | Stachler | ............ | A62B 17/04 2/424 |
| 2011/0219506 A1 | 9/2011 | Uttrachi | | |
| 2014/0298557 A1 * | 10/2014 | Townsend, Jr. | ............ | A61F 9/06 2/8.2 |
| 2015/0033431 A1 | 2/2015 | Hofer Kraner et al. | | |
| 2016/0360821 A1 * | 12/2016 | Benton | ............ | A42B 3/226 |
| 2018/0110656 A1 * | 4/2018 | Ambring | ............ | A41D 13/0518 |

FOREIGN PATENT DOCUMENTS

| | | |
|---|---|---|
| CN | 104434394 A | 3/2015 |
| CN | 204766130 U | 11/2015 |
| EP | 1862199 A2 | 12/2007 |
| EP | 2839817 A1 | 2/2015 |
| GB | 1511303 A | 5/1978 |

OTHER PUBLICATIONS

Extended European Search Report regarding Application No. 15896910.5, dated Aug. 13, 2018, 8 pages.

IP Australia Examination report No. 1 for standard patent application regarding Application No. 2015400937, dated Jun. 5, 2019, 3 pages.

Ip Australia Examination report No. 2 for standard patent application regarding Application No. 2015400937, dated Jan. 6, 2020, 3 pages.

* cited by examiner

WELDING HELMET HAVING A ZIPPER ARRANGEMENT AND WELDING HELMET ASSEMBLY

CROSS-REFERENCE TO RELATED APPLICATIONS

This patent application is the U.S. national phase of International Patent Application No. PCT/CN2015/088738, filed Sep. 1, 2015, which claims the benefit of Chinese Patent Application No. 201510383611.3, filed on Jul. 2, 2015, which are incorporated by reference in their entireties herein.

FIELD

The present application generally relates to a welding helmet, especially an auto-darkening welding helmet, which is equipped with a detachable head cover by a zipper arrangement to guarantee air tightness of air supply for the welding helmet.

BACKGROUND

When carrying out a welding operation, an operator usually wears a welding helmet on his/her head to prevent him/her from being hurt by spattering matters and various harmful rays caused by welding-arc ignition.

Conventionally, the welding helmet, for example an auto-darkening welding helmet, is equipped with an auto-darkening filter (ADF). The auto-darkening filter is mainly provided with a liquid crystal panel. The liquid crystal panel is transparent in case of no welding-arc ignition. The liquid crystal panel is converted into an opaque state just before the welding-arc ignition begins, such that the operator's eyes are protected. The auto-darkening welding helmet is usually provided with an adjustable knob or button. Before wearing the welding helmet, the operator can set operating parameters, such as SENSITIVITY, delay time, shade, and weld mode or the like, of the auto-darkening filter by the knob or button. Thereafter, the operator can wear the welding helmet to carry out the welding operation.

In order to enable the operator to work on a severe or harmful welding site, the welding helmet is also equipped with an air supplying device. The air supplying device is connected to the welding helmet by a conduit. In order to guarantee air tightness of air supply, the welding helmet is detachably connected to a head cover. The head cover can be enclosed about the operator's head. The head cover is made of a flexible material. Usually, the head cover is coupled to the welding helmet using a Velcro such that the head cover can be detached or washed as desired.

Although the Velcro between the head cover and the welding helmet can ensure a detachable coupling therebetween, the Velcro itself cannot guarantee qualified air tightness of the air supply. Even, after being disconnected or connected for a long term, the Velcro is prone to disengagement. If this happens, the operator wearing the welding helmet will not be necessarily protected under the harmful working condition. Therefore, there is a need to develop new technical means by which the air tightness between the head cover and the welding helmet can be guaranteed and a long-term, reliable and detachable coupling therebetween can be also achieved.

SUMMARY

With respect to the shortcomings in the prior art, the present application is aimed at proposing an improved welding helmet whose head cover can be repeatedly and reliably disconnected or connected without a risk of falling off and can provide better air impermeability than the Velcro.

According to one aspect of the present application, a welding helmet, especially an auto-darkening welding helmet, is provided, which comprises a helmet housing and a head cover adapted to be worn on a wearer's head and made of an air-impermeable and flexible material, wherein a zipper arrangement is provided between the helmet housing and the head cover to detachably connect the head cover to the helmet housing around the whole perimeter, or an entirety of an edge, of an opening of the helmet housing, and wherein after the head cover is connected to the helmet housing, the zipper arrangement is located within the housing of the welding helmet. According to the technical solution of the present application, the zipper arrangement ensures that the head cover can be assembled to or disassembled from the helmet housing for several times with the air impermeability being guaranteed therebetween.

Optionally, the zipper arrangement comprises a first unilateral zipper provided on an internal side of the helmet housing and a second unilateral zipper provided on the head cover and used to engage with the first unilateral zipper.

Optionally, the first unilateral zipper is securely bonded to the helmet housing and the second unilateral zipper is sewn on the head cover.

Optionally, a head cover fitting structure is securely bonded on the internal side of the helmet housing around the whole perimeter of the opening, and the first unilateral zipper is sewn on the head cover fitting structure.

Optionally, the head cover fitting structure is in the form of a loop-shaped sheet around the whole perimeter of the opening, which sheet has a profile conforming to the internal profile of the helmet housing. The head cover fitting structure is configured in such a way that the wearing comfort of the wearer cannot be affected.

Optionally, the zipper of the zipper arrangement is a metal or plastic zipper.

Optionally, a flexible strip of protective cloth is provided on the internal side of the helmet housing or an internal side of the head cover, and after the head cover is connected to the helmet housing, the strip of protective cloth covers the zipper arrangement. The flexible strip of protective cloth further improves the wearing comfort of the wearer.

Optionally, a layer of seal coating is applied on the zipper arrangement to guarantee its air impermeability.

Optionally, the head cover is made of a flexible and air-impermeable material, for example an air-impermeable cloth fabric.

According to another aspect of the present application, a welding helmet assembly, especially an auto-darkening welding helmet assembly, is provided, which comprises a welding helmet as recited previously, an air supplying device, and an air feeding hose connected between the air supplying device and the welding helmet, wherein air can be fed to the welding helmet through the air feeding hose.

BRIEF DESCRIPTION OF THE DRAWINGS

The forgoing and other aspects of the present application will be well understood by the following description in combination with the drawings. It should be noted that although those drawings may be given in different proportions, they cannot be deemed to affect understanding of the present application. In the drawings.

DETAILED DESCRIPTION

Figure 1:
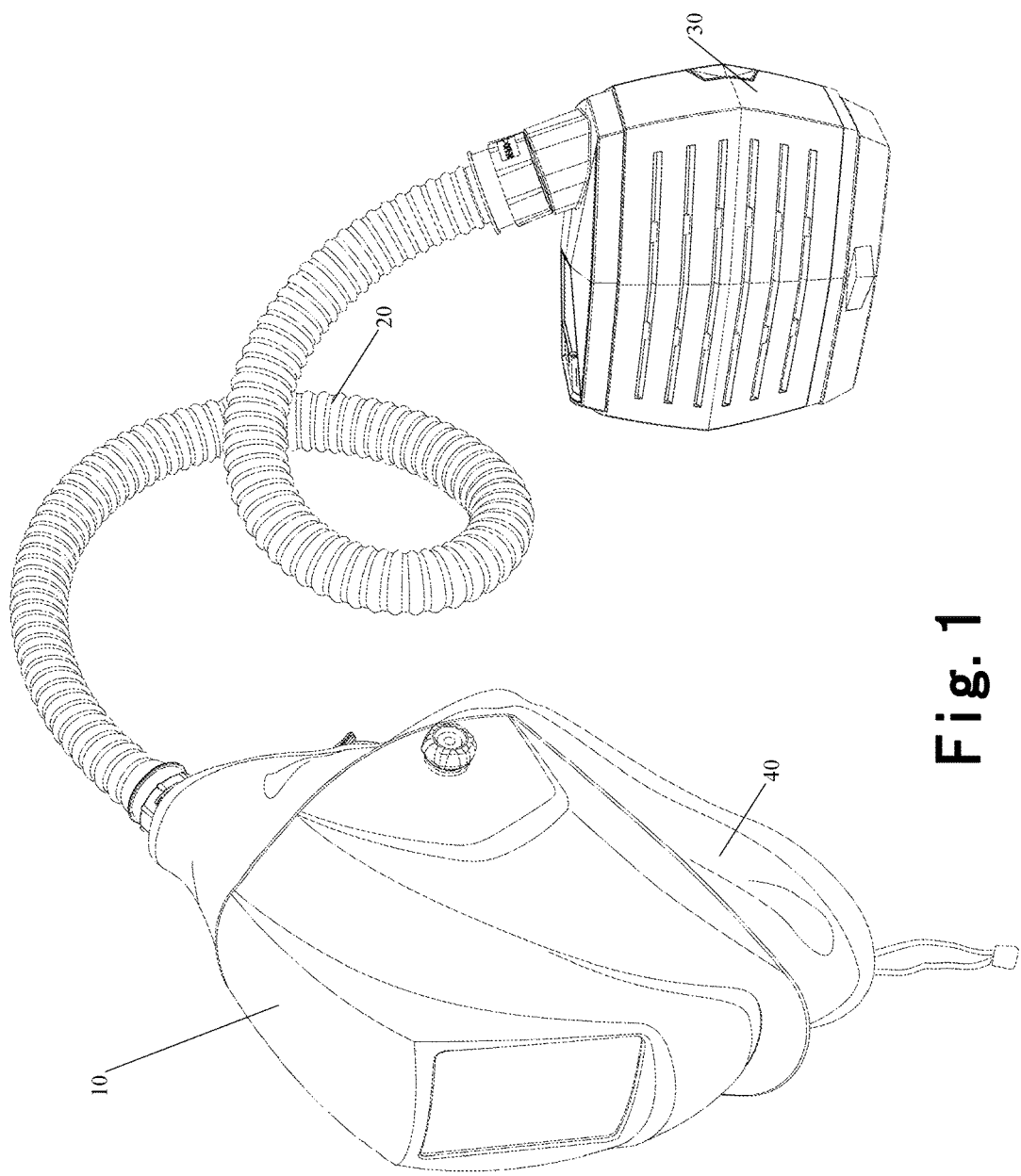
FIG. 1 is a schematic view illustrating a welding helmet, especially an auto-darkening welding helmet, equipped with an air-supplying device.

In the drawings of the present application, features having the same configuration or similar functions are represented by the same reference numerals.

FIG. 1 illustrates a welding helmet 10. This welding helmet 10 is installed with a head cover 40 thereon. The welding helmet 10 is also equipped with an air-supplying device 30. An air feeding hose 20 is connected between the welding helmet 10 and the air supplying device 30. The welding helmet 10, the head cover 40, the air supplying device 30 and the air feeding hose 20 constitute a welding helmet assembly.

After an operator wears the welding helmet 10 on his/her head, the head cover 40 wraps around the head. The air supplying device 30 is placed on the operator's waist. The air supplying device can be actuated, as required on a welding site such that air can be supplied to the interior of the welding helmet 10 through the air feeding hose 20.

It should be noted that in the context of the present application, the welding helmet 10 may be any type of welding helmet, for example an auto-darkening welding helmet. Below, take the auto-darkening welding helmet for example to explain it.

Further, as shown in FIG. 1, one end of the air feeding hose 20 is connected to the head cover 40 installed on the welding helmet 10. However, it can be appreciated that the end of the air feeding hose 20 can be designed such that its end can be connected directly to the welding helmet 10.

Figure 2:
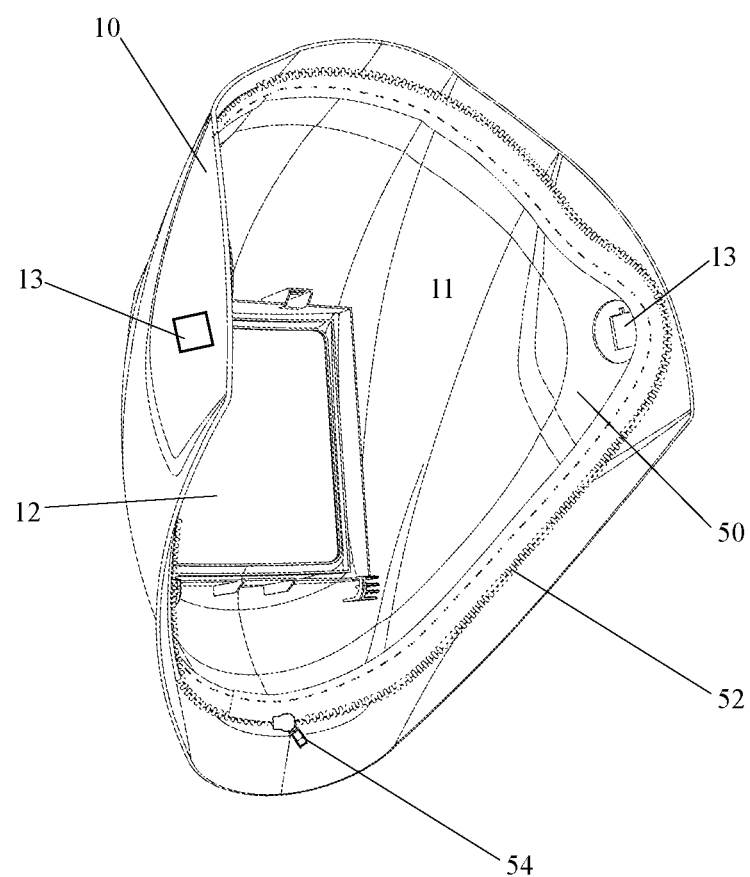
FIG. 2 is a perspective view which is observed from the interior of the welding helmet shown in FIG. 1.

FIG. 2 is a perspective view which is observed from an internal side of the welding helmet of FIG. 1. It should be noted that in the context of the present application, the term "internal side" refers to a side facing the operator's head after the welding helmet is worn on his/her head; and the term "external side" refers to a side departing from the operator's head after the welding helmet is worn on his/her head.

The welding helmet 10 comprises a housing 11. For example, the housing 11 is made of a hard plastic material. An auto-darkening filter 12 is installed on the housing 11 to protect the operator's eyes in welding-arc ignition. A mounting hole 13 is opened on either lateral side of the housing 11 substantially adjacent to one ear of the operator wearing the helmet, by which mounting hole a headband structure (not shown) adapted for the housing 11 of the welding helmet 10 can be mounted. The headband structure is located at an internal side of the housing 11 and can be worn directly on the operator's head to secure the welding helmet 10.

Figure 3:
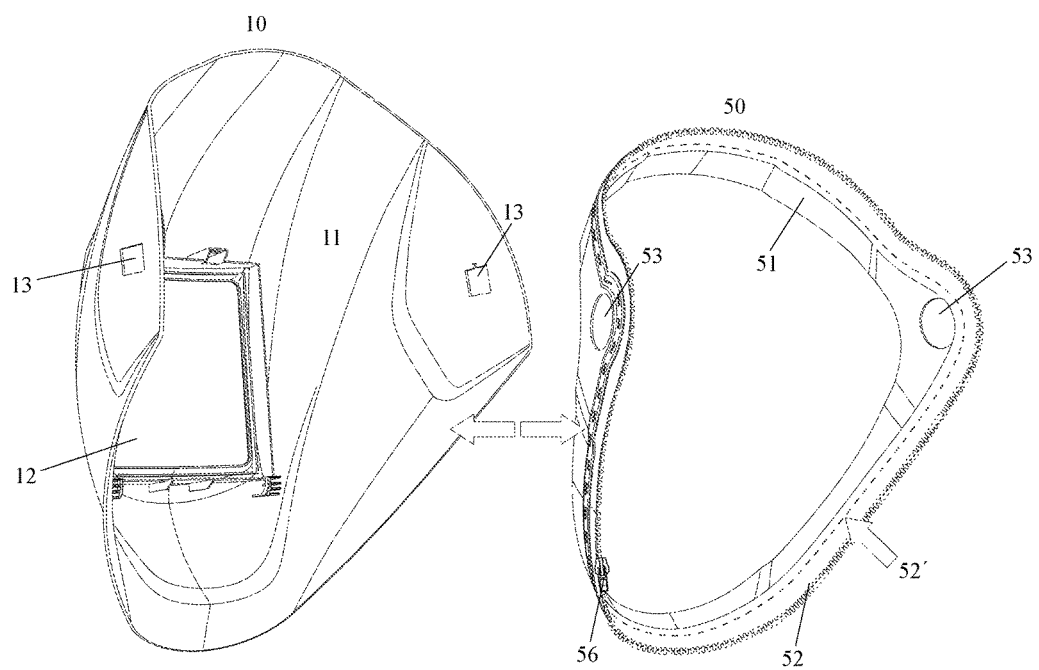
FIG. 3 is an exploded view illustrating how to assemble the welding helmet of FIG. 2.

According to the present application, as shown in FIGS. 2 and 3, a head cover fitting structure 50 is installed on the internal side of the housing 11 of the welding helmet 10. The head cover fitting structure 50 is used to be detachably connected to the head cover 40. It should be understood that after being assembled together, the head cover fitting structure 50 is located between the internal side of the housing 11 and the (not shown) headband structure.

The head cover fitting structure 50 comprises a body 51 made of a flexible material, for example a flexible plastic material. The body 51 is substantially in the form of a loop-shaped sheet, whose shape matches that of the internal side of the housing 11 adjacent to its outer edge. In this way, after the body 51 contacts the internal side of the housing 11, the body 51 is located substantially in the internal side adjacent to the outer edge such that it is perfectly attachable over the profile of the internal side of the housing 11 without any excessive embossing. Two eyeholes 53 are provided in the body 51. After being assembled in place, the eyeholes 53 are in communication with the respective mounting holes 13 such that the headband structure can be installed by them.

As shown in FIGS. 2 and 3, a unilateral zipper 52 is sewn on the internal side of the body 51 along its whole circumference. As an alternative, it is also feasible to sew the unilateral zipper 52 onto an external side of the body 51. When the welding helmet 10 is assembled, the external side of the plastic body 51 is first coated uniformly with a layer of an adhesive, such as any suitable adhesive which is known by the skilled person to bond plastics; and then the body 51 is bonded directly to the internal side of the housing 11, as shown in FIG. 2, such that the unilateral zipper 52 on the plastic body 51 can be lifted up freely. The plastic body 51 is bonded uniformly on the internal side of the housing 11 such that air cannot leak from them.

Figure 4:
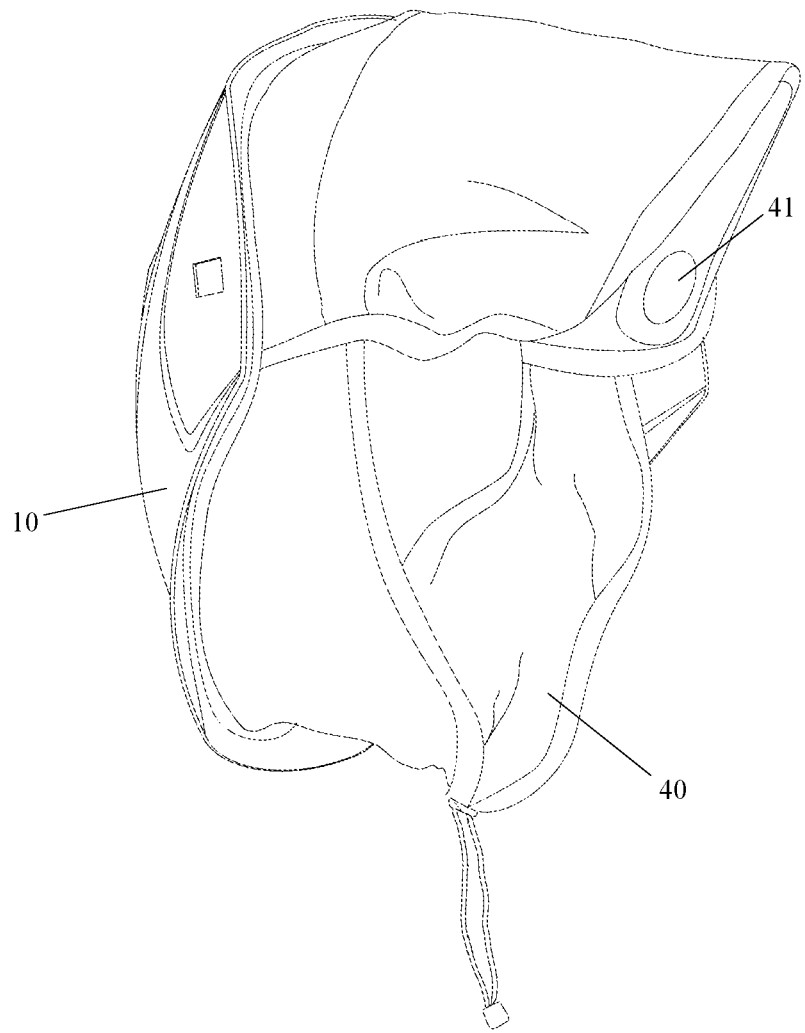
FIG. 4 is a perspective view illustrating that the welding helmet of FIGS. 2 and 3 is equipped with a head cover.

Now, the head cover 40 according to the present application and its installation on the welding helmet 10 will be explained with respect to FIGS. 4 and 5 below. The head cover 40 is made of a flexible and air-impermeable material, such as an air-impermeable cloth fabric and can be wrapped on the operator's head to protect him/her under a severe working condition. Further, under this condition, due to the head cover, air supplied by the air-supplying device 30 can be inhaled by the operator. For instance, an opening 41 is provided in the head cover 40 to connect an end of the air feeding hose 20, as shown in FIG. 1, to feed air therethrough.

At an edge of the head cover 40 for connecting the welding helmet 10, a unilateral zipper 42 is sewn, whose length is equal to the length of the unilateral zipper 52 as shown in FIG. 3 and which is configured in such a way that it is complementary to the zipper 52. Since the unilateral zipper 52 is just located adjacent to the internal edge of the housing 11, it is feasible for the operator to pull a zipper head 56 provided on the unilateral zipper 50 by his/her finger, during assembling, to enable the two unilateral zippers 42 and 52 to engage with each other. In this way, the head cover 40 can be connected to the welding helmet 10. A pull tab 54 of the zipper head is located at an external side of the head cover 40 and the head cover fitting structure 50 and thus is readily accessible by the operator's finger to disassemble them. According to the present application, the two unilateral zippers 42 and 52 and the zipper head 56 constitute a detachable mounting structure, especially a zipper arrangement, between the welding helmet 10 and the head cover 40.

This zipper arrangement can be any suitable zipper arrangement known by the skilled person in the art, for example a plastic or metal zipper arrangement or the like. After the assembled welding helmet 10 has been worn on the operator's head, the zipper arrangement between the welding helmet 10 and the head cover 40 is just located around the operator's face. The zipper arrangement can achieve better air impermeability than a Velcro according to the prior art. Even if the zipper arrangement is engaged or disengaged for several times, no risk of falling off or air impermeability becoming bad may occur. Therefore, a wearer, who wears the welding helmet on his/her head, can be reliably protected in the severe working condition where he/she carries out a welding operation.

Figure 5:
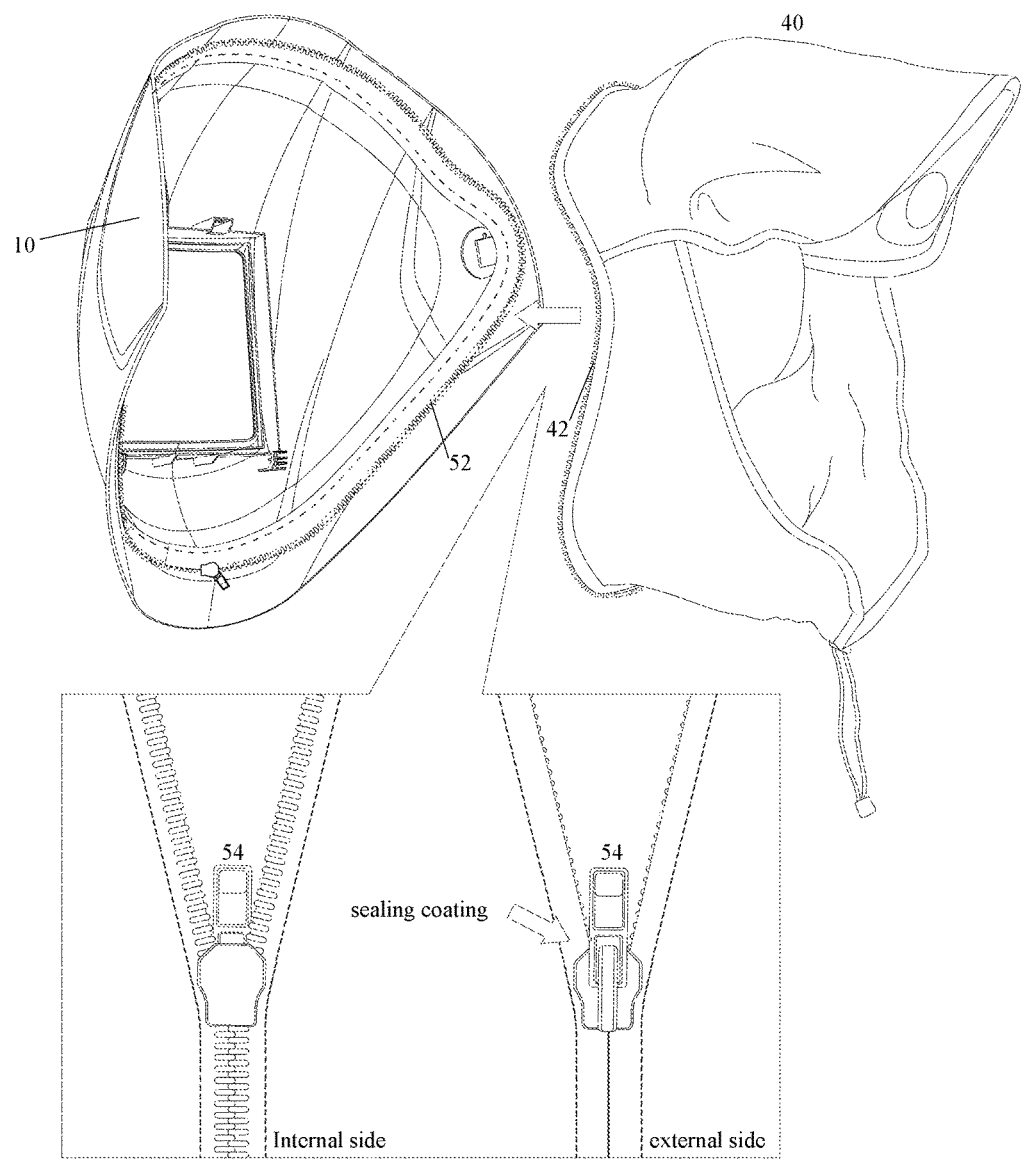
FIG. 5 is an exploded view illustrating how to assemble the welding helmet of FIG. 4 with the head cover.

As shown in FIG. 5, in order to guarantee the better air impermeability of the zipper arrangement, the zipper arrangement can be applied with a layer of seal coating, such as a waterproof sealing layer, on its external side (for example, the side where the pull tab 54 is located) beforehand, such that air is impermeable and the zipper arrangement cannot be permeated by the operator's sweat.

Since the zipper arrangement according to the present application may be in direct contact with the operator's face after the welding helmet 10 is worn on his/her head, a flexible strip of cloth can be sewn on a side of the zipper arrangement for contacting the operator's face such that the helmet can be worn more comfortably. For instance, as shown in FIG. 3, one edge of the flexible strip of cloth can be sewn on the unilateral zipper 52 by a seam line 52' and the other opposite edge is exposed outwards. Moreover, the strip of cloth has a length equal to that of the unilateral zipper 52 and a width greater than or equal to the sum of those of the unilateral zippers 42 and 52. Therefore, after the two unilateral zippers 42 and 52 engage each other, the strip of cloth covers the zippers 42 and 52 at a side intending to contact the operator's face. That is to say, it is not the zipper arrangement but the flexible strip of cloth that is in direct contact with the operator's face such that the wearer will feel more comfortable. Moreover, since the flexible strip of cloth covers the zipper arrangement, the air impermeability of the zipper arrangement is improved further.

It is conceived by the skilled person in the art that the zipper head 54 illustrated by FIG. 3 can be alternatively provided on the unilateral zipper 42 of the head cover 40. Furthermore, it is conceived that in an embodiment of the present application, the head cover fitting structure 50 can be omitted. In this case, the unilateral zipper 52 can be bonded to the internal side of the housing 11 by a suitable adhesive at one edge and, at the same time, the unilateral zipper 52 is enabled to be lifted up freely at the other edge having zipper. In this way, the zipper arrangement can be also formed by this unilateral zipper engaging with the matchable unilateral zipper 42 on the head cover 40.

Although some concrete embodiments of the present application have been explained, they are given for illustrative purposes only and cannot be deemed to give any limitation to the scope of the present application. Various alternations, modifications and renovations can be thought out without departing from the spirit and scope of the present application.

The invention claimed is:

1. A welding helmet, comprising:
a helmet housing adapted to cover a face of a wearer, the helmet housing comprising an opening adapted for a head of the wearer and a headband mounting hole;
a head cover fitting structure provided on an internal side of the helmet housing and comprising a hole aligned with the headband mounting hole;
a head cover adapted to be worn on the head of the wearer and cover a top and a rear of the head of the wearer, the head cover comprising an air-impermeable and flexible material; and
a zipper arrangement provided between the helmet housing and the head cover to detachably connect the head cover to the helmet housing around an entirety of an edge of the opening of the helmet housing, the zipper arrangement comprising:
a first unilateral zipper provided on the head cover fitting structure on the internal side of the helmet housing, and
a second unilateral zipper complementary to the first unilateral zipper and provided on the head cover to engage with the first unilateral zipper, the second unilateral zipper being on an internal side of the head cover when engaged with the first unilateral zipper,
wherein after the head cover is connected to the helmet housing, the zipper arrangement is located within the helmet housing.

2. The welding helmet of claim 1, wherein:
the zipper arrangement further comprises a zipper head configured to engage with the first unilateral zipper and the second unilateral zipper, and
a zipper tab of the zipper head is provided on an external side of the head cover opposite the first unilateral zipper and the second unilateral zipper.

3. The welding helmet of claim 2, wherein the first unilateral zipper is bonded to the head cover fitting structure and the second unilateral zipper is sewn on the head cover.

4. The welding helmet of claim 2, wherein:
the head cover fitting structure is bonded on the internal side of the helmet housing around the entirety of the edge of the opening of the helmet housing; and
the first unilateral zipper is sewn on the head cover fitting structure.

5. The welding helmet of claim 4, wherein:
the head cover fitting structure is in a form of a loop-shaped sheet around the entirety of the edge of the opening of the helmet housing, and
the loop-shaped sheet comprises a profile conforming to an internal profile of the helmet housing.

6. The welding helmet of claim 1, wherein the zipper arrangement includes a zipper comprising metal or plastic.

7. The welding helmet of claim 1, further comprising a flexible strip of protective cloth provided on the internal side of the helmet housing or the internal side of the head cover,
wherein after the head cover is connected to the helmet housing, the strip of protective cloth covers the zipper arrangement.

8. The welding helmet of claim 1, wherein a layer of seal coating is applied on the zipper arrangement.

9. The welding helmet of claim 1, wherein the head cover comprises an air-impermeable cloth fabric.

10. The welding helmet of claim 1, wherein the welding helmet is an auto-darkening welding helmet.

11. The welding helmet of claim 1, wherein the head cover fitting structure comprises a flexible plastic material.

12. A welding helmet assembly comprising:
a welding helmet comprising:
a helmet housing adapted to cover a face of a wearer, the helmet housing comprising an opening adapted for a head of the wearer and a headband mounting hole,
a head cover fitting structure provided on an internal side of the helmet housing and comprising a hole aligned with the headband mounting hole,
a head cover adapted to be worn on the head of the wearer and cover a top and a rear of the head of the wearer, the head cover comprising an air-impermeable and flexible material, and
a zipper arrangement provided between the helmet housing and the head cover to detachably connect the head cover to the helmet housing around an entirety of an edge of the opening of the helmet housing, wherein after the head cover is connected to the helmet housing the zipper arrangement is located within the helmet housing, the zipper arrangement comprising:
- a first unilateral zipper provided on the head cover fitting structure on the internal side of the helmet housing, and
- a second unilateral zipper complementary to the first unilateral zipper and provided on the head cover to engage with the first unilateral zipper, the second unilateral zipper being on an internal side of the head cover when engaged with the first unilateral zipper, an air supplying device; and an air feeding hose including a first end connected to the air supplying device and a second end connected to the welding helmet, wherein the air feeding hose is configured to feed air from the air supplying device to the welding helmet.

13. The welding helmet assembly of claim 12, wherein the welding helmet is an auto-darkening welding helmet.

14. The welding helmet assembly of claim 12, wherein:
the zipper arrangement further comprises a zipper head configured to engage with the first unilateral zipper and the second unilateral zipper, and
a zipper tab of the zipper head is provided on an external side of the head cover opposite the first unilateral zipper and the second unilateral zipper.

15. The welding helmet assembly of claim 12, wherein the head cover fitting structure comprises a flexible plastic material.

* * * * *